(12) United States Patent
Kuma et al.

(10) Patent No.: US 6,207,735 B1
(45) Date of Patent: Mar. 27, 2001

(54) FLAME RETARDANT AND FLAME RETARDANT RESIN COMPOSITION CONTAINING IT

(75) Inventors: Kimitaka Kuma; Kenji Koyama, both of Shinnanyo; Fumio Okizaki; Yasumi Tanaka, both of Yokkaichi, all of (JP)

(73) Assignee: Tosch Corporation, Yamaguchi-ken (JP)

( * ) Notice: Subject to any disclaimer, the term of this patent is extended or adjusted under 35 U.S.C. 154(b) by 0 days.

(21) Appl. No.: 09/205,225

(22) Filed: Dec. 4, 1998

(30) Foreign Application Priority Data

| Dec. 8, 1997 | (JP) | 9-336989 |
| Dec. 8, 1997 | (JP) | 9-336990 |
| Dec. 11, 1997 | (JP) | 9-341498 |
| Dec. 11, 1997 | (JP) | 9-341499 |

(51) Int. Cl.$^7$ .................................................. C08K 5/34
(52) U.S. Cl. ........................ 524/100; 524/101; 524/204
(58) Field of Search ...................................... 524/204, 101, 524/100

(56) References Cited

U.S. PATENT DOCUMENTS 5,498,476 * 3/1996 Tucker et al. ...................... 524/140
5,994,435 * 11/1999 Kuma et al. ........................ 524/204

OTHER PUBLICATIONS

Derwent Publications Ltd., London, GB; AN 97–389417 XP002097809 & JP 09 169784A (Tosoh Corp), Jun. 30, 1997.

\* cited by examiner

*Primary Examiner*—Veronica P. Hoke
(74) *Attorney, Agent, or Firm*—Sughrue, Mion, Zinn, Macpeak & Seas, PLLC (57) ABSTRACT

A flame retardant comprising (A) ethylenediamine-containing zinc phosphate and (B) a metal compound.

22 Claims, 2 Drawing Sheets

FLAME RETARDANT AND FLAME RETARDANT RESIN COMPOSITION CONTAINING IT

FIELD OF THE INVENTION

The present invention relates to a flame retardant and a flame retardant resin composition containing it. The flame retardant and the flame retardant resin composition containing it according to the present invention, are of high performance having excellent flame retardancy, smoke suppressant properties and generating no hazardous gas, and they are useful in a wide range as materials for, e.g., various electric parts, automobile parts, building materials, cables and wire harnesses.

BACKGROUND OF THE INVENTION

Although plastic materials are used in many industrial applications, because of their inflammability, flame retardants are formulated to plastic materials in order to afford them flame retardancy.

Conventional flame retardants include, for example, a phosphorus-containing compound such as a phosphoric acid ester, ammonium polyphosphate or red phosphorus, a halogen-containing compound such as tetrabromobisphenol A, decabromodiphenyloxide or chlorinated paraffin, and a metal compound such as magnesium hydroxide, aluminum hydroxide or zinc borate. Among these, a halogen-containing compound is excellent in flame retardancy and is widely used.

However, a resin formulated with a halogen-containing compound has problems of releasing hazardous halogen-containing gas and generating much smoke on combustion. Generation of hazardous gas and smoke increases the risk of physical disaster danger at the time of fire. Accordingly, safety of the material is an important technology along with the technology for flame retardancy.

Although a phosphorus-containing compound is a material that generates little smoke, for example, ammonium polyphosphate is not necessarily satisfactory from the viewpoint of flame retardancy and water resistance.

Further, a metal compound represented by magnesium hydroxide releases no hazardous gas during thermal decomposition and is a material excellent in the smoke suppressant effect. However, it is not necessarily satisfactory from the viewpoint of the flame retardancy.

The present invention has been made in view of the above problems, and it is an object of the present invention to provide a new high performance flame retardant having an excellent flame retardant and smoke suppressant effect, and a new flame retardant resin composition containing it.

The present inventors have conducted an extensive study to develop a high performance flame retardant to obtain a flame retardant resin composition excellent in flame retardancy and smoke suppressant effect, and as a result, have succeeded in accomplishing the present invention.

SUMMARY OF THE INVENTION

Namely, the present invention provides a flame retardant comprising (A) ethylenediamine-containing zinc phosphate and (B) a metal compound; a flame retardant comprising (A) ethylenediamine-containing zinc phosphate, (B) a metal compound, and (C) a 1,3,5-triazine derivative and/or (D) a phosphorus-containing compound; and a flame retardant comprising (A) ethylenediamine-containing zinc phosphate, (C) a 1,3,5-triazine derivative, and (D) a phosphorus-containing compound; and a flame retardant resin composition containing such a flame retardant.

BRIEF DESCRIPTION OF THE DRAWINGS

In the accompanying drawings.

Now, the present invention will be described in detail.

DESCRIPTION OF THE PREFERRED EMBODIMENTS

Firstly, the flame retardant of the present invention will be described.

The flame retardant of the present invention is a flame retardant comprising (A) ethylenediamine-containing zinc phosphate and (B) a metal compound; a flame retardant comprising (A) ethylenediamine-containing zinc phosphate, (B) a metal compound, and (C) a 1,3,5-triazine derivative and/or (D) a phosphorus-containing compound; or a flame retardant comprising (A) ethylenediamine-containing zinc phosphate, (C) a 1,3,5-triazine derivative, and (D) a phosphorus-containing compound.

In the present invention, the ethylenediamine-containing zinc phosphate is not particularly limited so long as it is a compound of ethylenediamine with zinc phosphate. For example, it may be ethylenediamine-containing zinc phosphate represented by the general formula $Zn_2P_2O_8C_2N_2H_{10}$ and of which the X-ray diffraction pattern contains at least the spacings shown in Table 1:

TABLE 1

| X-ray diffraction positions of ethylenediamine-containing zinc phosphate | | |
|---|---|---|
| Spacing d (Å) | 2 θ | Relative intensity |
| 7.32 ± 0.50 | 12.1 | S to M |
| 5.66 ± 0.16 | 15.6 | M |
| 4.46 ± 0.10 | 19.9 | M |
| 4.10 ± 0.10 | 21.7 | W |
| 3.81 ± 0.08 | 23.3 | S to M |
| 3.39 ± 0.07 | 26.2 | VS |
| 3.28 ± 0.05 | 27.2 | S |
| 2.76 ± 0.04 | 32.4 | W |
| 2.73 ± 0.04 | 32.8 | W |
| 2.65 ± 0.04 | 33.8 | W |
| 2.60 ± 0.04 | 34.5 | W |
| 2.31 ± 0.04 | 38.9 | W |
| 2.21 ± 0.04 | 40.9 | W |

2θ: measured by CuKα radiation (1.5405 Å) In the relative intensity, VS: very strong, S: strong, M: medium, and W: weak; or ethylenediamine-containing zinc phosphate, of which the X-ray diffraction pattern contains at least the spacings shown in Table 2:

TABLE 2

X-ray diffraction positions of ethylenediamine-
containing zinc phosphate

| Spacing d (Å) | 2 θ | Relative intensity |
| --- | --- | --- |
| 6.89 ± 0.30 | 12.8 | VS |
| 6.66 ± 0.30 | 13.3 | S |
| 4.20 ± 0.10 | 21.1 | W |
| 4.09 ± 0.10 | 21.7 | S to M |
| 3.79 ± 0.08 | 23.4 | S |
| 3.38 ± 0.07 | 26.3 | S |
| 3.32 ± 0.05 | 26.8 | W |
| 3.14 ± 0.05 | 28.4 | M |
| 2.82 ± 0.04 | 31.7 | M |
| 2.74 ± 0.04 | 32.6 | S to M |
| 2.70 ± 0.04 | 33.1 | M |
| 2.60 ± 0.04 | 34.4 | W |

2θ: measured by CuKα radiation (1.5405 Å) In the relative intensity, VS: very strong, S: strong, M: medium, and W: weak.

Figure 1:
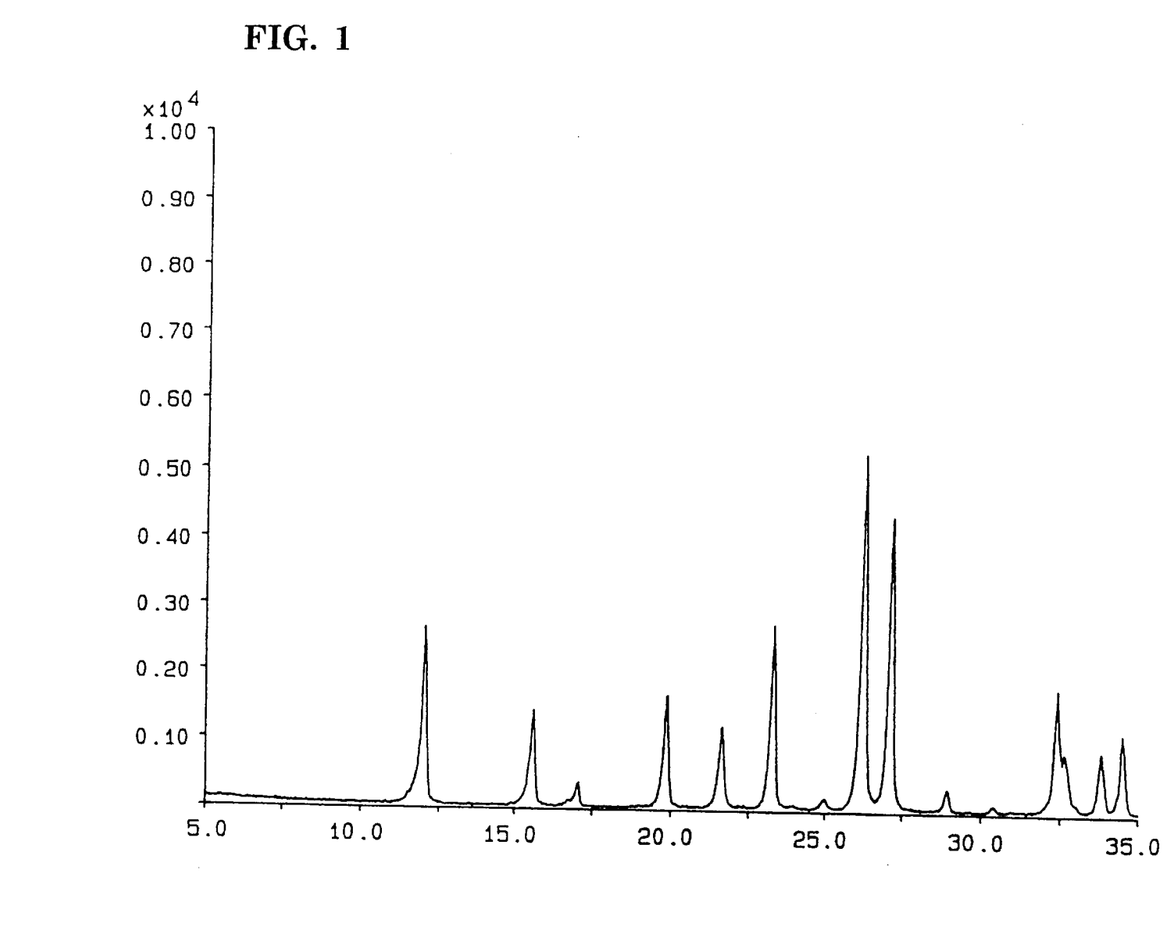
FIG. 1 shows the X-ray diffraction pattern of the ethylenediamine-containing zinc phosphate obtained in Preparation Example 1.

The ethylenediamine-containing zinc phosphate represented by the general formula of $Zn_2P_2O_8C_2N_2H_{10}$ and of which the X-ray diffraction pattern contains at least the spacings shown in the above Table 1, is a three dimensional open framework zinc phosphate. The structure is based on a network of $ZnO_4$ and $PO_4$ tetrahedra. The charge neutrality of $ZnPO_4^-$ is achieved by incorporation of $H_3NC_2H_3NH_3^{2+}$, and its X-ray diffraction pattern measured by means of CuKα radiation is as shown in FIG. 1 (R. H. Jones et al, Studies in Surface Science and Catalysis, Zeolites and Related Microporous Materials, Vol. 84, p. 2229 (1994), Elsevier Science B.V.).

Figure 2:
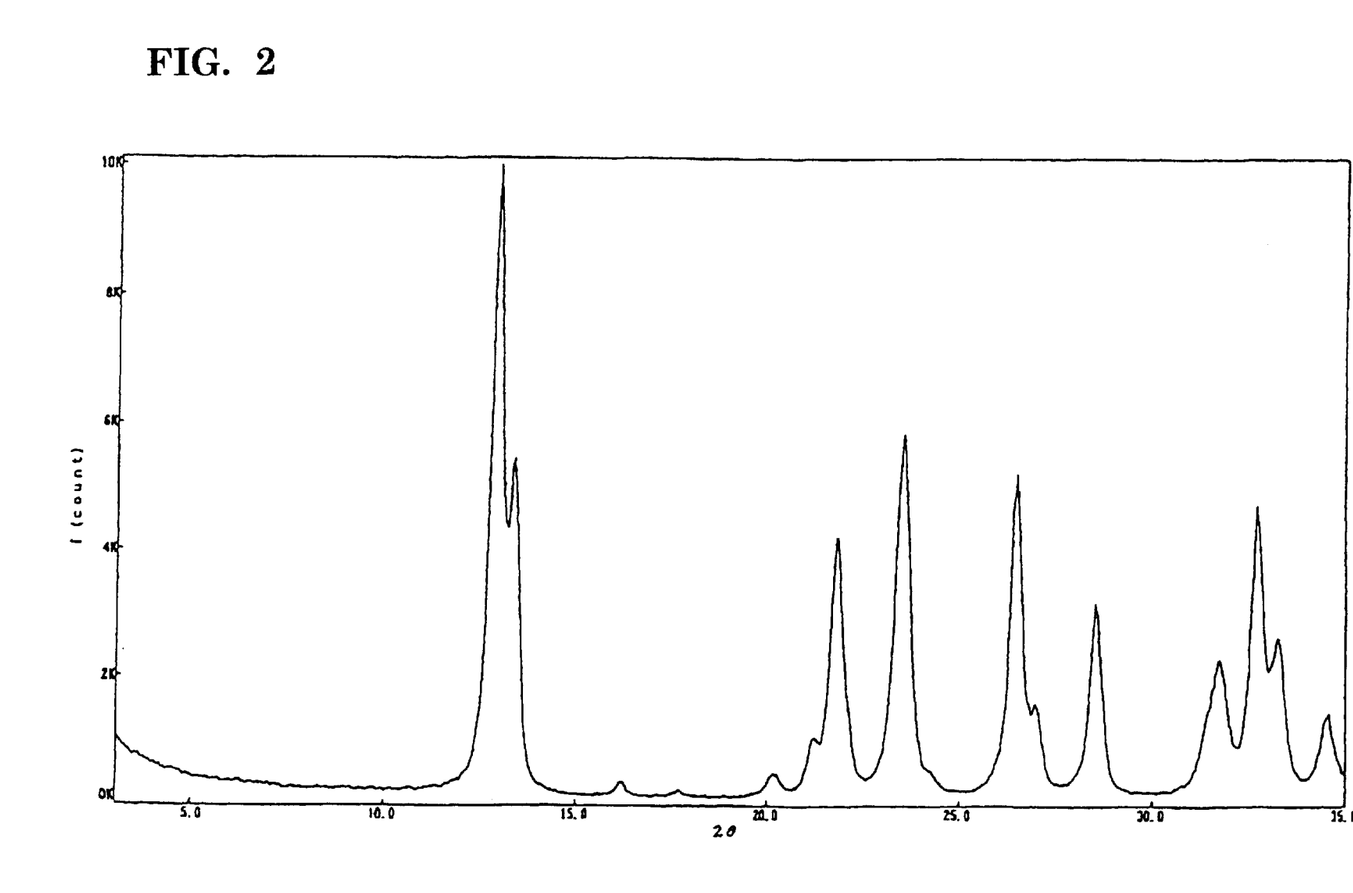
FIG. 2 shows the X-ray diffraction pattern of the ethylenediamine-containing zinc phosphate obtained in Preparation Example 11.

With respect to the ethylenediamine-containing zinc phosphate, of which the X-ray diffraction pattern contains at least the spacings shown in the above Table 2, the detailed crystal structure is not known, but the X-ray diffraction pattern measured by means of CuKα radiation is as shown in FIG. 2.

The ethylenediamine-containing zinc phosphate to be used in the present invention has a decomposition temperature of about 400° C. and is a material excellent in heat resistance. The powder properties are not particularly limited, but the BET specific surface area is preferably from 0.1 to 20 m²/g, and the secondary particle size is preferably around 20 μm or smaller.

Now, a method for producing the ethylenediamine-containing zinc phosphate will be described. However, the production method is not particularly limited, and a preferred embodiment will be described.

The ethylenediamine-containing zinc phosphate of the present invention is produced via each step of crystallization, filtration, washing, drying and pulverization of ethylenediamine-containing zinc phosphate.

In the case of the ethylenediamine-containing zinc phosphate represented by the general formula of $Zn_2P_2O_8C_2N_2H_{10}$ and of which the X-ray diffraction pattern contains at least the spacings shown in the above Table 1, the crystallization is carried out by mixing an aqueous zinc phosphate solution and an aqueous ethylenediamine solution.

At that time, the aqueous zinc phosphate solution is prepared usually by mixing a compound of zinc with phosphoric acid in such amounts that the molar ratio of phosphorus/zinc would be from 2.5 to 10.0 thereby uniformly dissolving the compound of zinc.

The compound of zinc may be, for example, an inorganic acid salt such as zinc sulfate, zinc nitrate, zinc chloride, zinc acetate or zinc perchlorate, an organic acid salt such as zinc benzoate, zinc citrate, zinc formate, zinc lactate, zinc oleate or zinc salicylate, zinc metal, zinc oxide or zinc hydroxide, and it is not particularly limited. The concentration of the aqueous zinc phosphate solution is not particularly limited, and the zinc concentration and the phosphorus concentration may be at a level of from a few tens to a few thousands mmol/l. The concentration of the aqueous ethylenediamine solution is not particularly limited and may be at a level of from a few tens to a few thousands mmol/l.

The mixing of the aqueous zinc phosphate solution with the aqueous ethylenediamine solution may be carried out in such amounts that the molar ratio of ethylenediamine/zinc would be 0.5 to 2.0. The mixing method is not particularly limited, and it may be a method of adding the aqueous ethylenediamine solution to the aqueous zinc phosphate solution, a method of adding the aqueous zinc phosphate solution to the aqueous ethylenediamine solution, or a method of continuously adding the aqueous zinc phosphate solution and ethylenediamine into a reactor. The mixing is preferably carried out with stirring to make the inside of the reactor homogeneous. In the case where the aqueous ethylenediamine solution is added to the aqueous zinc phosphate solution, or the aqueous zinc phosphate solution is added to the aqueous ethylenediamine solution, the time for adding the aqueous solution, may be from a few minutes to a few hours. The temperature during the mixing may be from 5 to 90° C., and the time for homogenizing may be from 5 minutes to 3 days.

The present inventors have further found a method for economically producing the ethylenediamine-containing zinc phosphate represented by the general formula of $Zn_2P_2O_8C_2N_2H_{10}$ and of which the X-ray diffraction pattern contains at least the spacings shown in the above Table 1, without using ethylenediamine and phosphoric acid more than necessary. Such a method will now be described.

In this case, the crystallization is carried out by mixing an aqueous zinc phosphate solution having a phosphorus/zinc molar ratio of from 1.0 to 2.0 with an aqueous ethylenediamine solution in an amount such that the molar ratio of ethylenediamine/zinc would be from 0.5 to 1.0, then adjusting the pH to a level of from 3 to 11, followed by aging. The phosphorus/zinc molar ratio of the aqueous zinc phosphate solution is from 1.0 to 2.0, preferably from 1.0 to 1.5, more preferably from 1.0 to 1.2. If the phosphorus/zinc molar ratio is less than 1.0, impurities other than the ethylenediamine-containing zinc phosphate will be included in the product. On the other hand, if the phosphorus/zinc molar ratio exceeds 2.0, the amount of unreacted phosphoric acid tends to be large, such being uneconomical.

When the aqueous zinc phosphate solution is to be prepared, there may be a case where depending upon its nature, the zinc compound will not uniformly dissolve in the aqueous phosphoric acid solution. In such a case, the zinc compound may be dissolved by using phosphoric acid in combination with an acid other than phosphoric acid. As the acid other than phosphoric acid, hydrochloric acid, nitric acid or sulfuric acid may, for example, be mentioned, but it is not limited to such a specific acid. The amount of the acid other than phosphoric acid is not particularly limited and may be an amount whereby the zinc compound can uniformly be dissolved. The zinc compound which requires use of the acid other than phosphoric acid, may, for example, be zinc metal, zinc oxide or zinc hydroxide.

Then, this aqueous zinc phosphate solution and the aqueous ethylenediamine solution are mixed in such amounts that the molar ratio of ethylenediamine/zinc would be from 0.5 to 1.0, preferably from 0.5 to 0.8, more preferably from 0.5 to 0.6. If the molar ratio of ethylenediamine/zinc is less than 0.5, impurities other than ethylenediamine-containing zinc phosphate will be included in the product. On the other hand, if the molar ratio of ethylenediamine/zinc exceeds 1.0, the amount of unreacted ethylenediamine tends to be large, such being uneconomical.

The temperature during the mixing is preferably from 0 to 50° C., to prevent inclusion of impurities other than ethylenediamine-containing zinc phosphate or for economical production.

After mixing the aqueous zinc phosphate solution and the aqueous ethylenediamine solution, the pH is adjusted to a level of from 3 to 11. The pH of the mixture obtained by mixing the aqueous zinc phosphate solution and the aqueous ethylenediamine solution is about 2, and at such a pH level, the solubility of the ethylenediamine-containing zinc phosphate is large, whereby the yield of the resulting ethylenediamine-containing zinc phosphate tends to be low. Accordingly, adjustment of the pH is carried out to increase the yield of ethylenediamine-containing zinc phosphate, and is an essential step for the process of the present invention.

The pH is adjusted to a range of from 3 to 11, particularly preferably within a range of from 4 to 10. If the adjusted pH is less than 3 or exceeds 11, the effect for improving the yield of ethylenediamine-containing zinc phosphate tends to be small, and impurities other than ethylenediamine-containing zinc phosphate tend to be included in the product.

The method for adjusting the pH to a level of from 3 to 11 is not particularly limited. The pH may be adjusted by adding an alkali such as a powder or an aqueous solution of, e.g., sodium hydroxide, potassium hydroxide or urea, or a gas or an aqueous solution of, e.g., ammonia, to a mixture obtained by mixing the aqueous zinc phosphate solution and the aqueous ethylenediamine solution.

Further, depending upon the adjusted pH, the pH may decrease in the subsequent aging step. The adjustment of pH in the present invention is carried out so that the pH is maintained within the above-mentioned range of from 3 to 11 also in the aging step. The temperature for adjusting the pH is preferably from 0 to 50° C.

After adjusting the pH, aging is carried out. In the present invention, the aging is a step wherein stirring is continued to mix and make the slurry homogeneous. The aging time is not particularly limited, but is usually from a few minutes to a few tens hours, preferably from 3 to 24 hours. The aging temperature is preferably from 0 to 50° C.

The present inventors have conducted extensive research for a process which is capable of synthesizing fine ethylenediamine-containing zinc phosphate in order to prevent deterioration of the mechanical properties of the resin composition containing the ethylenediamine-containing zinc phosphate, and, as a result, have found a process for producing ethylenediamine-containing zinc phosphate which is represented by the general formula of $Zn_2P_2O_8C_2N_2H_{10}$ and of which the X-ray diffraction pattern contains at least the spacings as shown in the above Table 1, and the particle size is less than 4 $\mu$m. The process will be described as follows.

In this case, the crystallization is carried out by maintaining the temperature of less than 40° C. during adjusting the pH and aging, in the above-mentioned economical process for producing ethylenediamine-containing zinc phosphate.

Namely, after mixing the aqueous zinc phosphate solution having a phosphorus/zinc molar ratio of from 1.0 to 2.0, with the aqueous ethylenediamine solution in such an amount that the molar ratio of ethylenediamine/zinc would be from 0.5 to 1.0, the pH is adjusted to a level of from 3 to 11 at a temperature of less than 40° C., followed by aging at a temperature of less than 40° C. In the present invention, the particle size means an average particle size measured with a particle size analyzer by means of a light scattering method.

The temperature during adjusting the pH and aging is not particularly limited, but is preferably less than 40° C., more preferably less than 35° C. If the temperature at the time of adjusting the pH and aging exceeds 40° C., it tends to obtain ethylenediamine-containing zinc phosphate having a particle size exceeding 4 $\mu$m.

Now, a preferred embodiment will be described with respect to a process for producing ethylenediamine-containing zinc phosphate, of which the X-ray diffraction pattern contains at least the spacings shown in the above Table 2.

In this case, the crystallization is carried out by mixing an aqueous zinc salt solution with ethylenediamine to form tris(ethylenediamine)zinc(II) and reacting the tris (ethylenediamine)zinc(II) with phosphoric acid.

The method for producing the tris(ethylenediamine)zinc (II) is not particularly limited. For example, it can be obtained by mixing an aqueous zinc salt solution with ethylenediamine in a molar ratio of 1/3 with stirring at a temperature of from 5 to 90° C. The concentration of the aqueous zinc salt solution is usually a few mol/l, and as the zinc salt, a water-soluble salt such as zinc nitrate, zinc chloride or zinc sulfate may, for example, be mentioned.

The reaction of aqueous solution of tris(ethylenediamine) zinc(II) with phosphoric acid can be carried out at a mixing ratio of tris(ethylenediamine)zinc(II)/phosphoric acid of from 0.5 to 2.0 (molar ratio). The mixing is preferably carried out while stirring to maintain the inside of the reactor homogeneous. The temperature during the mixing may be from 5 to 90° C., and the time for homogenizing may be at a level of from 5 minutes to 3 days.

After the ethylenediamine-containing zinc phosphate was crystallized, the crystals of ethylenediamine-containing zinc phosphate were subjected to solid-liquid separation, followed by washing. The method for solid-liquid separation is not particularly limited, and Nutsche filter, rotary drum filter, filter press, horizontal band filter, etc., may, for example, be mentioned. The amount of washing water is not particularly limited, and washing may be carried out until unreacted phosphoric acid and ethylenediamine have been removed.

Then, drying of the crystals of ethylenediamine-containing zinc phosphate is carried out. The temperature for the drying is not particularly limited and may be within a range of from 60 to 250° C.

The dried ethylenediamine-containing zinc phosphate is further pulverized slightly, if need be. The pulverization method is not particularly limited, and pulverization may be carried out, for example, by a rotary crusher or a hammer crusher, etc.

The ethylenediamine-containing zinc phosphate of the present invention can be produced by the above-described processes.

In the present invention, the metal compound may be at least one member selected from the group consisting of a metal hydroxide and a metal oxide. The metal hydroxide may, for example, be magnesium hydroxide, aluminum hydroxide, calcium hydroxide and zinc hydroxystannate. The metal oxide may, for example, be nickel oxide, cobalt oxide, iron oxide, antimony trioxide, antimony pentoxide, copper oxide, molybdenum oxide, tin oxide, zinc borate, zinc stannate or a zeolite.

In the present invention, the 1,3,5-triazine derivative is not particularly limited so long as it has a 1,3,5-triazine skeleton. For example, it may be 1,3,5-triazine, melamine, methylol-modified melamine (iso)cyanuric acid, its salts with basic chemical, e.g., melamine, and alkyl or aryl esters of (iso)cyanuric acid.

In the present invention, the phosphorus-containing compound is a phosphorus-containing compound other than the above-described ethylenediamine-containing zinc phosphate and is not particularly limited. For example, it may be red phosphorus, ammonium polyphosphate, a phosphoric acid ester, melamine phosphate, melamine polyphosphate, guanidine phosphate or an ethylenediamine phosphate. In the present invention, the ethylenediamine phosphate means a salt of ethylenediamine with phosphoric acid and is not particularly limited. For example, it may be synthesized by the method disclosed in J. Amer. Chem. Soc., 77, 6513 (1955).

In the present invention, the formulating ratio of (A) ethylenediamine-containing zinc phosphate and (B) a metal compound is not particularly limited. However, the one with a formulating ratio of (A) the ethylenediamine-containing zinc phosphate to (B) the metal compound of from 0.1 to 10 by weight ratio, exhibits excellent flame retardancy and thus is particularly preferred. The formulating ratio of the total amount of (A) the ethylenediamine-containing zinc phosphate and (B) the metal compound to (C) the 1,3,5-triazine derivative and/or (D) the phosphorus-containing compound, is not particularly limited, but one with such a formulating ratio of from 0.1 to 10 by weight ratio, exhibits excellent flame retardancy, and thus is particularly preferred. Further, the formulating ratio of the total amount of (A) the ethylenediamine-containing zinc phosphate and (D) the phosphorus-containing compound to the amount of (C) the 1,3,5-triazine derivative, is not particularly limited, but one having such a ratio of from 0.1 to 10 by weight ratio, exhibits excellent flame retardancy and is particularly preferred.

Now, the flame retardant resin composition of the present invention will be described.

The flame retardant resin composition of the present invention is a composition formulated with 5 to 250 parts by weight, particularly preferably 20 to 200 parts by weight, of the present inventive flame retardant to 100 parts by weight of resin. If the amount of the flame retardant of the present invention is less than 5 parts by weight, the flame retardancy tends to be inadequate, and if it exceeds 250 parts by weight, the mechanical properties of the resin tend to deteriorate in some cases.

The resin may be used without any particular restriction, depending upon the particular purpose. For example, it may be a polyolefin which is a homopolymer or copolymer of an olefinic monomer, such as polyethylene, polypropylene, an ethylene-propylene copolymer, an ethylene-propylene-diene monomer three component copolymer, an ethylene-ethyl acrylate copolymer or an ethylene-vinyl acetate copolymer, a polystyrene which is a homopolymer or copolymer made essentially of vinyl aromatic monomer, such as a styrene homopolymer, a rubber-modified polystyrene, or a graft polymer of rubber with acrylonitrile or (meth)acrylate with styrene, a poly(meth)acrylic resin, a polyester such a polyethylene terephthalate, a polybutylene terephthalate or a polyallylate, a polyamide such as 6-nylon, 6,6-nylon, 12-nylon, 46-nylon or an aromatic polyamide, a polyether such as a polyphenylene ether, a modified polyphenylene ether, a polyoxymethylene, a polycarbonate, or a styrene-conjugated diene copolymer, a rubber such as a polybutadiene, a polyisoprene, an acrylonitrile-butadiene copolymer or a polychloroprene, or a polyvinyl chloride. Further, a thermosetting resin such as a phenol resin, an epoxy resin, a vinylester resin, an unsaturated polyester or a polyurethane, may also be mentioned. These resins may be used alone or in combination as a mixture of two or more of them.

The method of formulating the flame retardant of the present invention to such a resin may be such that the respective components of the flame retardant may preliminarily be complexed and formulated to the resin, or they may separately be formulated to the resin. The method for complexing is not particularly limited, but may be carried out by a wet or dry method with, for example, a ball mill or vibration mill using balls made of zirconia or urethane resin, a drum mixer, twin cylinder mixer, etc. The mixing time may be from a few hours to a few tens of hours.

As the kneaders for formulating the flame retardant to resin, a mixing roll, sigma-type kneader, Banbury mixer, screw type extruder are mentioned, but such are not particularly limited, and formulation can be carried out by a method suitable for the resin to be used.

The flame retardant resin composition of the present invention can be produced by the above-described method.

To the flame retardant resin composition of the present invention, other additives may be formulated, as the case requires. The additives include, for example, other flame retardants, flame-retarding aids, plasticizers, lubricants, fillers, antioxidants, heat stabilizers, crosslinking agents, crosslinking aids, antistatic agents, compatabilizing agents, light retardant agents, pigments, foaming agents, antimold agents, etc.

The flame retardant of the present invention comprising the ethylenediamine-containing zinc phosphate and the metal compound, or the ethylenediamine-containing zinc phosphate, the metal compound and the 1,3,5-triazine derivative and/or the phosphorus-containing compound, or the ethylenediamine-containing zinc phosphate, the 1,3,5-triazine derivative and the phosphorus-containing compound, is excellent in the flame retardancy, and the flame retardant resin composition of the present invention formulated with it is of high performance having excellent flame retardancy, smoke suppressant properties and generating no hazardous gas.

Now, the present invention will be described in further detail with reference to Examples. However, it should be understood that the present invention is by no means restricted to such specific Examples.

PREPARATION EXAMPLE 1

Preparation of ethylenediamine-containing zinc phosphate 7,000 g of water and 484 g of 85% phosphoric acid were mixed, and 1,150 g of zinc sulfate heptahydrate was dissolved therein to obtain an aqueous zinc phosphate solution having a phosphorus/zinc molar ratio of 1.05.

To the above aqueous zinc phosphate solution, an aqueous ethylenediamine solution prepared by mixing 7,000 g of water and 126 g of ethylenediamine, was added (molar ratio of ethylenediamine/zinc=0.53), and the pH was adjusted to 8 with a 10% sodium hydroxide aqueous solution, followed by aging at 30° C. for 5 hours to obtain an ethylenediamine-containing zinc phosphate slurry. The ethylenediamine-containing zinc phosphate slurry was subjected to solid-liquid separation by Nutsche, washed with 50,000 g of water and then dried at 90° C. for 16 hours.

The particle size of the ethylenediamine-containing zinc phosphate was measured in accordance with the following method. The ethylenediamine-containing zinc phosphate was added to water and subjected to ultrasonic dispersion for 10 minutes. The particle size was measured by using "MICROTRAC FRA9200" manufactured by LEEDS & NORTHRUP COMPANY.

The particle size of the obtained ethylenediamine-containing zinc phosphate was 3.5 μm, and the yield was 99%. The X-ray diffraction pattern appeared at positions indicated in Table 1, and the X-ray diffraction pattern measured with CuKα radiation is shown in FIG. 1.

PREPARATION EXAMPLE 2

Preparation of ethylenediamine-containing zinc phosphate 7,000 g of water and 553 g of 85% phosphoric acid were mixed, and 1,190 g of zinc nitrate hexahydrate was dissolved therein to obtain an aqueous zinc phosphate solution having a phosphorus/zinc molar ratio of 1.20.

To the above aqueous zinc phosphate solution, an aqueous ethylenediamine solution prepared by mixing 7,000 g of water and 144 g of ethylenediamine, was added (molar ratio of ethylenediamine/zinc=0.60), and the pH was adjusted to 8 with a 10% sodium hydroxide aqueous solution, followed by aging at 40° C. for 24 hours, then, in the same manner as in Preparation Example 1, solid-liquid separation, washing and drying were carried out.

The particle size of the obtained ethylenediamine-containing zinc phosphate was measured in the same manner as in Preparation Example 1. The particle size was 7.0 μm, the yield was 99%, and the X-ray diffraction pattern appeared at the positions shown in Table 1.

PREPARATION EXAMPLE 3

Preparation of ethylenediamine-containing zinc phosphate 7,000 g of water and 553 g of 85% phosphoric acid were mixed, and 545 g of zinc chloride was dissolved therein to obtain an aqueous zinc phosphate solution having a phosphorus/zinc molar ratio of 1.20.

The above aqueous zinc phosphate solution was added to an aqueous ethylenediamine solution prepared in the same manner as in Preparation Example 2, and the pH was adjusted to 8 with a 10% sodium hydroxide aqueous solution, followed by aging at 45° C. for 24 hours. Then, in the same manner as in Preparation Example 1, solid-liquid separation, washing and drying were carried out.

The particle size of the obtained ethylenediamine-containing zinc phosphate was measured in the same manner as in Preparation Example 1. The particle size was 10.1 μm, the yield was 99%, and the X-ray diffraction pattern appeared at positions shown in Table 1.

PREPARATION EXAMPLE 4

Preparation of ethylenediamine-containing zinc phosphate

An aqueous ethylenediamine solution prepared in the same manner as in Preparation Example 2 was added to an aqueous zinc phosphate solution prepared in the same manner as in Preparation Example 1, then the pH was adjusted to 9 with a 10% sodium hydroxide aqueous solution, followed by aging at 30° C. for 16 hours. Further, in the same manner as in Preparation Example 1, solid-liquid separation, washing and drying were carried out.

The particle size of the obtained ethylenediamine-containing zinc phosphate was measured in the same manner as in Preparation Example 1. The particle size was 3.0 μm, the yield was 99%, and the X-ray diffraction pattern appeared at positions shown in Table 1.

PREPARATION EXAMPLE 5

Preparation of ethylenediamine-containing zinc phosphate 607 g of 97% sulfuric acid and 507 g of 85% phosphoric acid were mixed to 7,000 g of water, and 326 g of zinc oxide was added and dissolved therein to obtain an aqueous zinc phosphate solution having a phosphorus/zinc molar ratio of 1.10.

To the above aqueous zinc phosphate solution, an aqueous ethylenediamine solution prepared by mixing 7,000 g of water and 132 g of ethylenediamine, was added (molar ratio of ethylenediamine/zinc=0.55), and the pH was adjusted to 8 with a 10% sodium hydroxide aqueous solution, followed by aging at 30° C. for 5 hours. Then, in the same manner as in Preparation Example 1, solid-liquid separation, washing and drying were carried out.

The particle size of the obtained ethylenediamine-containing zinc phosphate was measured in the same manner as in Preparation Example 1. The particle size was 3.4 μm, the yield was 99%, and the X-ray diffraction pattern appeared at positions shown in Table 1.

PREPARATION EXAMPLE 6

Preparation of ethylenediamine-containing zinc phosphate

An aqueous zinc phosphate solution prepared in the same manner as in Preparation Example 1 was added to an aqueous ethylenediamine solution prepared in the same manner as in Preparation Example 1, and the pH was adjusted to 8 with a 10% sodium hydroxide aqueous solution while maintaining the temperature at 10° C., followed by aging at 10° C. for 5 hours. In the same manner as in Preparation Example 1, solid-liquid separation, washing and drying were carried out.

The particle size of the obtained ethylenediamine-containing zinc phosphate was measured in the same manner as in Preparation Example 1. The particle size was 2.2 μm, the yield was 99%, and the X-ray diffraction pattern appeared at positions shown in Table 1.

PREPARATION EXAMPLE 7

Preparation of ethylenediamine-containing zinc phosphate

An aqueous ethylenediamine solution prepared in the same manner as in Preparation Example 2 were added to an aqueous zinc phosphate solution prepared in the same manner as in Preparation Example 1, and the pH was adjusted to 9 with a 10% sodium hydroxide aqueous solution while maintaining the temperature at 15° C., followed by aging at 15° C. for 16 hours. Then, in the same manner as in Preparation Example 1, solid-liquid separation, washing and drying were carried out.

The particle size of the obtained ethylenediamine-containing zinc phosphate was measured in the same manner as in Preparation Example 1. The particle size was 2.7 μm, the yield was 99%, and the X-ray diffraction pattern appeared at positions shown in Table 1.

PREPARATION EXAMPLE 8

Preparation of ethylenediamine-containing zinc phosphate

An aqueous ethylenediamine solution was added in the same manner as in Preparation Example 1 to an aqueous zinc phosphate solution prepared in the same manner Preparation Example 1, and the pH was adjusted to 8.0 with a 48% sodium hydroxide aqueous solution while maintaining the temperature at 5° C., followed by aging at a temperature of 5° C. for 5 hours. Then, in the same manner as in Preparation Example 1, solid-liquid separation, washing and drying were carried out to obtain ethylenediamine-containing zinc phosphate.

The particle size of the obtained ethylenediamine-containing zinc phosphate was measured in the same manner as in Preparation Example 1. The particle size was 2.0 μm, the yield was 99%, and the X-ray diffraction pattern appeared at positions shown in Table 1.

PREPARATION EXAMPLE 9

Preparation of ethylenediamine-containing zinc phosphate

An aqueous ethylenediamine solution was added in the same manner as in Preparation Example 1 to an aqueous zinc phosphate solution prepared in the same manner as in Preparation Example 1, and the pH was adjusted to 8 with a 48% sodium hydroxide aqueous solution while maintaining the temperature at 50° C., followed by aging at 50° C. for 5 hours. Then, in the same manner as in Preparation Example 1, solid-liquid separation, washing and drying were carried out.

The particle size of the obtained ethylenediamine-containing zinc phosphate was measured in the same manner as in Preparation Example 1. The particle size was 4.7 μm, the yield was 99%, and the X-ray diffraction pattern appeared at positions shown in Table 1.

PREPARATION EXAMPLE 10

Preparation of ethylenediamine-containing zinc phosphate

An aqueous ethylenediamine solution was added in the same manner as in Preparation Example 1 to an aqueous zinc phosphate solution prepared in the same manner as in Preparation Example 1, and the pH was adjusted 9.7 with a 48% sodium hydroxide aqueous solution while maintaining the temperature at 15° C., followed by aging at 15° C. for 5 hours. Then, in the same manner as in Preparation Example 1, solid-liquid separation, washing and drying were carried out to obtain ethylenediamine-containing zinc phosphate.

The particle size of the obtained ethylenediamine-containing zinc phosphate was measured in the same manner as in Preparation Example 1. The particle size was 1.1 μm, the yield was 99%, and the X-ray diffraction pattern appeared at positions shown in Table 1.

PREPARATION EXAMPLE 11

Preparation of ethylenediamine-containing zinc phosphate 59.5 g of zinc nitrate hexahydrate was dissolved in 540 g of water, and to this aqueous zinc nitrate solution, 36 g of ethylenediamine was added to obtain an aqueous tris(ethylenediamine)zinc(II) solution.

An aqueous phosphoric acid solution prepared by adding 23.1 g of 85% phosphoric acid to 180 g of water, was added to the above aqueous tris(ethylenediamine)zinc(II) solution, and the slurry was homogenized at 30° C. for 1 hour to crystallize ethylenediamine-containing zinc phosphate. After the crystallization, it was subjected to solid-liquid separation by Nutsche filtration, followed by washing with 3,000 g of water and then drying at 110° C. for 16 hours to obtain ethylenediamine-containing zinc phosphate. The X-ray diffraction of the ethylenediamine-containing zinc phosphate appeared at positions shown in Table 2, and the X-ray diffraction pattern is shown in FIG. 2.

PREPARATION EXAMPLE 12

Preparation of Flame Retardants 1 to 3

The ethylenediamine-containing zinc phosphate prepared in Preparation Example 1, ammonium polyphosphate ("HOSTAFLAM AP462", tradename, manufactured by Hoechst) and melamine cyanurate ("MC-440", tradename, manufactured by Nissan Chemical) were mixed in weight ratios of 2:1:1, 1:1:1 and 1:2:1, to obtain flame retardants 1 to 3 respectively.

PREPARATION EXAMPLE 13

Preparation of Flame Retardants 4 to 6

The ethylenediamine-containing zinc phosphate prepared in Preparation Example 1, melamine phosphate ("MPP-2", tradename, manufactured by Sanwa Chemical) and melamine cyanurate ("MC-440", tradename, manufactured by Nissan Chemical) were mixed in weight ratios of 2:1:1, 1:1:1, and 1:2:1, to obtain flame retardants 4 to 6 respectively.

PREPARATION EXAMPLE 14

Preparation of Flame Retardants 7 to 9

The ethylenediamine-containing zinc phosphate prepared in Preparation Example 1 and magnesium hydroxide ("Kisma 5B", tradename, manufactured by Kyowa Chemical) were mixed in weight ratios of 2:1, 1:1, and 1:2, to obtain flame retardants 7 to 9 respectively.

PREPARATION EXAMPLE 15

Preparation of Flame Retardants 10 to 12

The ethylenediamine-containing zinc phosphate prepared in Preparation Example 1, zinc borate ("Zinc Borate 2335", tradename, manufactured by Tomita Seiyaku) and melamine cyanurate ("MC-440", tradename, manufactured by Nissan Chemical) were mixed in weight ratios of 2:1:1, 1:1:1, and 1:2:1, to obtain flame retardants 10 to 12 respectively.

PREPARATION EXAMPLE 16

Preparation of Flame Retardants 13 to 15

The ethylenediamine-containing zinc phosphate prepared in Preparation Example 11, magnesium hydroxide ("Kisma 5B", tradename, manufactured by Kyowa Chemical) and melamine cyanurate ("MC-440", tradename, manufactured by Nissan Chemical) were mixed in weight ratios of 2:1:1, 1:1:1, and 1:2:1, to obtain flame retardants 13 to 15 respectively.

PREPARATION EXAMPLE 17

Preparation of Flame Retardants 16 to 18

The ethylenediamine-containing zinc phosphate prepared in Preparation Example 1, magnesium hydroxide ("Kisma 5B", tradename, manufactured by Kyowa Chemical) and ammonium polyphosphate ("HOSTAFLAM AP 462", tradename, manufactured by Hoechst) were mixed in weight ratios of 2:1:1, 1:1:1, and 1:2:1, to obtain flame retardants 16 to 18 respectively.

PREPARATION EXAMPLE 18

Preparation of Flame Retardants 19 to 22

The ethylenediamine-containing zinc phosphate prepared in Preparation Example 11, zinc borate ("Zinc Borate 2335", tradename, manufactured by Tomita Seiyaku) and red phosphorus ("Novared 120", tradename, manufactured by Rin Kagaku) were mixed in weight ratios of 5:1:1, 5:5:1, 1:1:1, and 1:5:1, to obtain flame retardants 19 to 22 respectively.

EXAMPLE 1

Evaluation of Flame Retardancy (1)

A flame retardant resin composition were prepared by formulating a predetermined amount of a flame retardant into an ethylene-ethyl acrylate copolymer ("Lextron EEA", tradename, Grade A1150, manufactured by Nippon Oil) under roll-mixing at 130° C. The resultant formulation was molded with press at 150° C. and then cut to the required test specimen specification.

Evaluation of the flame retardancy was determined by limiting oxygen index according to JIS K7201 and Underwrites Laboratory vertical burn test (UL94, thickness of specimen ⅛ inch).

The formulation level of the respective flame retardants and the results of evaluation of the flame retardancy of the respective flame retardant resin compositions are shown in Tables 3-1 to 3-2.

EXAMPLE 2

Evaluation of Flame Retardancy (2)

A flame retardant resin composition was prepared by formulating a predetermined amount of a flame retardant into a low-density polyethylene ("Petrocene 202", tradename, manufactured by TOSOH CORPORATION) under roll-mixing at 130° C. The resultant formulation was molded with press at 150° C. and then cut to the required test specimen specification.

Evaluation of the flame retardancy was carried out in the same method as in Example 1, and the formulation level of the respective flame retardants and the results of evaluation of the flame retardancy of the respective flame retardant resin compositions, are shown in Table 4.

EXAMPLE 3

Evaluation of Flame Retardancy (3) and Evaluation of Smoke Density

A flame retardant resin composition was prepared by formulating a predetermined amount of a flame retardant into an ethylene-vinyl acetate copolymer ("Ultracene 635", tradename, manufactured by TOSOH CORPORATION) under roll-mixing at 130° C. The resultant formulation was molded with press at 150° C. and then cut to the required test specimen specification.

Evaluation of the flame retardancy was carried out in the same manner as in Example 1, and the formulation level of the respective flame retardants, and the results of evaluation of the flame retardancy of the respective flame retardant resin compositions are shown in Table 5.

Optical density measurements on the smoke evolved from burning samples were carried out using a NBS-type Smoke Box. The formulation level of the respective flame retardants and the smoke densities of the respective flame retardant resin compositions are shown in the same Table 5.

EXAMPLE 4

Evaluation of the Mechanical Properties

60 Parts by weight of the ethylenediamine-containing zinc phosphate having an average particle size of 10.1 μm, prepared in Preparation Example 3, or the ethylenediamine-containing zinc phosphate having an average particle size of 2.0 μm, prepared in Preparation Example 8, was formulated to 100 parts by weight of an ethylene-ethyl acrylate copolymer ("Lextron EEA", tradename, Grade A1150, manufactured by Nippon Oil), and a flame retardant resin composition was prepared in the same manner as in Example 1.

Evaluation of the mechanical properties was carried out in accordance with the method prescribed in JIS K7113. The resin composition containing the ethylenediamine-containing zinc phosphate prepared in Preparation Example 3, had a breaking strength of 92 kg/cm$^2$ and a tensile elongation of 540%, and the resin composition containing the ethylenediamine-containing zinc phosphate prepared in Preparation Example 8, had a breaking strength of 103 kg/cm$^2$ and a tensile elongation of 680%.

COMPARATIVE EXAMPLE 1

Preparation of ethylenediamine-containing zinc phosphate 1,153 g of 85% phosphoric acid was mixed to 7,000 g of water, and 326 g of zinc oxide was added and dissolved therein to obtain an aqueous zinc phosphate solution having a phosphorus/zinc molar ratio of 2.50.

To the above aqueous zinc phosphate solution, an aqueous ethylenediamine solution prepared by mixing 7,000 g of water and 300 g of ethylenediamine, was added (molar ratio of ethylenediamine/zinc=1.25), followed by aging at 30° C. for 72 hours. Then, in the same manner as in Preparation Example 1, solid-liquid separation, washing and drying were carried out.

The particle size of the obtained ethylenediamine-containing zinc phosphate was measured in the same manner as in Preparation Example 1. The particle size was 4.4 μm, and the yield was 99%. However, unreacted phosphoric acid and ethylenediamine remained excessively in the filtrate. The X-ray diffraction pattern of the powder appeared at the positions shown in Table 1.

COMPARATIVE EXAMPLE 2

Preparation of ethylenediamine-containing zinc phosphate

An aqueous ethylenediamine solution prepared in the same manner as in Preparation Example 2 was added to an aqueous zinc phosphate solution prepared in the same manner as in Preparation Example 1, and the pH was adjusted to 8 with a 10% sodium hydroxide aqueous solution. Then, it was immediately subjected to solid-liquid separation by Nutsche, and in the same manner as in Preparation Example 1, washing and drying were carried out. In the product, a large amount of impurities were contained.

COMPARATIVE EXAMPLE 3

Preparation of ethylenediamine-containing zinc phosphate

An aqueous zinc phosphate solution prepared in the same manner as in Preparation Example 1, was added to an aqueous ethylenediamine solution prepared in the same manner as in Preparation Example 2, and without adjusting the pH, aging was carried out at 30° C. for 16 hours. Further, in the same manner as in Preparation Example 1, solid-liquid separation, washing and drying were carried out. The yield of the obtained ethylenediamine-containing zinc phosphate was 23%, and a large amount of impurities were contained in the product.

COMPARATIVE EXAMPLE 4

Preparation of ethylenediamine-containing zinc phosphate

An aqueous ethylenediamine solution prepared in the same manner as in Preparation Example 2 was added to an aqueous zinc phosphate solution prepared in the same manner as in Preparation Example 1, and the pH was adjusted to 13 with a 10% sodium hydroxide aqueous solution, followed by aging at 30° C. for 16 hours. Further, in the same manner as in Preparation Example 1, solid-liquid separation, washing and drying were carried out.

The product was zinc hydroxide only.

COMPARATIVE EXAMPLES 5 TO 15

Evaluation of Flame Retardancy

A predetermined amount of a flame retardant was formulated to an ethylene-vinyl acetate copolymer ("Ultracene 635", tradename, manufactured by TOSOH CORPORATION) in the same manner as in Example 1 to obtain a flame retardant resin composition. The formulation level of the respective flame retardants, and the results of evaluation of the flame retardancy of the respective flame retardant resin compositions are shown in Table 6.

COMPARATIVE EXAMPLES 16 TO 18

Evaluation of the Smoke Density

A predetermined amount of a flame retardant was formulated to an ethylene-vinyl acetate copolymer ("Ultracene 635", tradename, manufactured by TOSOH CORPORATION) in the same manner as in Example 1 to obtain a flame retardant resin composition, and evaluation of the smoke density was carried out in the same manner as in Example 3.

The formulation level of the respective flame retardants, and the results of evaluation of smoke density of the respective flame retardant resin compositions are shown in Table 7.

Here, evaluation of smoke density was carried out by the minimum amount of each flame retardant where the flame retardancy becomes to be V0 as evaluated by UL94V. It is evident that the flame retardants of the present invention are materials excellent in the smoke suppressant effects as compared with other flame retardants.

TABLE 3-1

Evaluation of flame retardancy
Resin : Ethylene-ethyl acrylate copolymer

| Flame retardant | Formulation level (phr) | Oxygen index (%) | UL94 |
|---|---|---|---|
| Flame retardant 1 | 30 | 29 | V1 |
| | 34 | 33 | V0 |
| Flame retardant 2 | 35 | 30 | V2 |
| | 38 | 32 | V0 |
| Flame retardant 3 | 35 | 29 | V2 |
| | 38 | 32 | V0 |
| Flame retardant 4 | 30 | 28 | V2 |
| | 35 | 32 | V0 |
| Flame retardant 5 | 35 | 33 | V0 |
| Flame retardant 6 | 40 | 32 | V0 |
| Flame retardant 7 | 50 | 29 | V2 |
| | 55 | 33 | V0 |
| Flame retardant 8 | 45 | 29 | V2 |
| | 48 | 34 | V0 |
| Flame retardant 9 | 45 | 27 | V2 |
| | 50 | 33 | V0 |

TABLE 3-2

Evaluation of flame retardancy
Resin : Ethylene-ethyl acrylate copolymer

| Flame retardant | Formulation level (phr) | Oxygen index (%) | UL94 |
|---|---|---|---|
| Flame retardant 10 | 35 | 35 | V0 |
| Flame retardant 11 | 35 | 36 | V0 |
| Flame retardant 12 | 38 | 36 | V0 |
| Flame retardant 13 | 40 | 31 | V2 |
| | 43 | 35 | V0 |
| Flame retardant 14 | 35 | 29 | V2 |
| | 38 | 34 | V0 |
| Flame retardant 15 | 35 | 30 | V2 |
| | 40 | 35 | V0 |
| Flame retardant 16 | 45 | 30 | V2 |
| Flame retardant 17 | 50 | 35 | V2 |
| Flame retardant 18 | 55 | 33 | V2 |
| Flame retardant 19 | 20 | 26 | V2 |
| | 25 | 28 | V1 |
| | 28 | 30 | V0 |
| Flame retardant 20 | 35 | 28 | V0 |
| Flame retardant 21 | 40 | 29 | V0 |
| Flame retardant 22 | 45 | 27 | V2 |

TABLE 4

Evaluation of flame retardancy
Resin : Low density polyethylene

| Flame retardant | Formulation level (phr) | Oxygen index (%) | UL94 |
|---|---|---|---|
| Flame retardant 1 | 30 | 26 | V2 |
| | 35 | 28 | V0 |
| Flame retardant 2 | 30 | 32 | V0 |

TABLE 4-continued

Evaluation of flame retardancy
Resin : Low density polyethylene

| Flame retardant | Formulation level (phr) | Oxygen index (%) | UL94 |
|---|---|---|---|
| Flame retardant 3 | 30 | 32 | V0 |
| Flame retardant 4 | 25 | 25 | V2 |
|  | 28 | 29 | V0 |
| Flame retardant 5 | 25 | 31 | V0 |
| Flame retardant 6 | 30 | 27 | V2 |
|  | 33 | 30 | V0 |
| Flame retardant 7 | 65 | 31 | V0 |
| Flame retardant 8 | 60 | 35 | V0 |
| Flame retardant 9 | 60 | 35 | V0 |
| Flame retardant 10 | 50 | 29 | V0 |
| Flame retardant 11 | 45 | 31 | V0 |
| Flame retardant 12 | 45 | 32 | V0 |
| Flame retardant 13 | 45 | 30 | V0 |
| Flame retardant 14 | 42 | 32 | V0 |
| Flame retardant 15 | 43 | 31 | V0 |

TABLE 5

Evaluation of flame retardancy
Resin : Ethylene-vinyl acetate copolymer

| Flame retardant | Formulation level (phr) | Oxygen index (%) | UL94 | Smoke density |
|---|---|---|---|---|
| Flame retardant 1 | 25 | 31 | V1 |  |
|  | 28 | 32 | V0 | 34 |
| Flame retardant 2 | 20 | 28 | V2 |  |
|  | 25 | 30 | V0 |  |
| Flame retardant 3 | 30 | 29 | V0 |  |
| Flame retardant 4 | 20 | 29 | V1 |  |
|  | 22 | 31 | V0 | 78 |
| Flame retardant 5 | 22 | 26 | V2 |  |
|  | 25 | 30 | V0 |  |
| Flame retardant 6 | 22 | 27 | V2 |  |
|  | 25 | 31 | V0 | 55 |
| Flame retardant 7 | 50 | 31 | V2 |  |
|  | 53 | 34 | V0 | 34 |
| Flame retardant 8 | 45 | 29 | V2 |  |
|  | 47 | 34 | V0 |  |
| Flame retardant 9 | 45 | 27 | V2 |  |
|  | 48 | 33 | V0 |  |
| Flame retardant 10 | 34 | 35 | V0 |  |
| Flame retardant 11 | 32 | 36 | V0 | 55 |
| Flame retardant 12 | 35 | 36 | V0 |  |
| Flame retardant 13 | 40 | 31 | V2 |  |
|  | 42 | 35 | V0 | 60 |
| Flame retardant 14 | 35 | 30 | V2 |  |
|  | 37 | 35 | V0 |  |
| Flame retardant 15 | 35 | 31 | V2 |  |
|  | 39 | 34 | V0 |  |
| Flame retardant 16 | 45 | 29 | V2 |  |
| Flame retardant 17 | 50 | 32 | V2 |  |
| Flame retardant 18 | 55 | 35 | V2 |  |

TABLE 6

Evaluation of flame retardancy
Resin : ethylene-vinyl acetate copolymer

| | Flame retardant (phr) | | | | | Oxygen index (%) | UL94 |
|---|---|---|---|---|---|---|---|
| | RP | APP | MH | ZB | MC | | |
| Comparative Example 5 | 40 | | | | | 23 | V0-V2 Fail to pass |
| Comparative Example 6 | | 50 | | | | 25 | V0-V2 Fail to pass |
| Comparative Example 7 | | | 55 | | | 24 | V0-V2 Fail to pass |
| Comparative Example 8 | | | | 45 | | 23 | V0-V2 Fail to pass |
| Comparative Example 9 | | | | | 40 | 24 | V0-V2 Fail to pass |
| Comparative Example 10 | 25 | | 25 | | | 23 | V0-V2 Fail to pass |
| Comparative Example 11 | | 25 | | 25 | | 24 | V0-V2 Fail to pass |
| Comparative Example 12 | | | 30 | 30 | | 23 | V0-V2 Fail to pass |
| Comparative Example 13 | 30 | 30 | | | | 25 | V0-V2 Fail to pass |
| Comparative Example 14 | | | 30 | 30 | | 26 | V0-V2 Fail to pass |

RP: Abbreviation of red phosphorus, "Novared 120", tradename, manufactured by Rin Kagaku
APP: Abbreviation of ammonium polyphosphate, "HOSTAFLAM AP 462", tradename, manufactured by Hoechst
MH: Abbreviation of magnesium hydroxide, "Kisma 5B", tradename, manufactured by Kyowa Chemical
MC: Abbreviation of melamine cyanurate, "MC-440", tradename, manufactured by Nissan Chemical
ZB: Abbreviation of zinc borate, "Zinc Borate 2335", tradename, manufactured by Tomita Seiyaku

TABLE 7

Evaluation of smoke density
(Comparative Examples 15 to 17)

| | Flame retardant | Formulation level (phr) | Smoke density |
|---|---|---|---|
| Comparative Example 15 | DBDE/Sb$_2$O$_3$ | 40 | 395 |
| Comparative Example 16 | MH/APP | 180 | 107 |
| Comparative Example 17 | EDAP | 67 | 184 |

DBDE/Sb$_2$O$_3$: A product obtained by mixing decabromodiphenyl oxide ("Flamecut 110R", manufactured by TOSOH CORPORATION) and Sb$_2$O$_3$ ("Flamecut 610R", manufactured by TOSOH CORPORATION) in a weight ratio of 3:1.
MH/APP: A product prepared by mixing magnesium oxide ("Kisma 5B", manufactured by Kyowa Chemical) and ammonium polyphosphate ("HOSTALAM AP 462", manufactured by Hoechst) in a weight ratio of 15:3.
EDAP: Abbreviation of ethylenediamine phosphate, prepared in accordance with J. Amer. Chem. Soc., 77, 6513 (1955).

What is claimed is:

1. A flame retardant comprising (A) ethylenediamine-containing zinc phosphate, (B) a metal compound and (C) a 1,3,5-triazine derivative and/or (D) a phosphorus-containing compound, wherein:

(B) the metal compound is at least one member selected from the group consisting of magnesium hydroxide, aluminum hydroxide, calcium hydroxide, zinc hydroxystannate, zinc oxide, nickel oxide, tin oxide, antimony oxide, zirconium oxide, molybdenum oxide, copper oxide, iron oxide, zinc borate, zinc stannate and zeolite;

(C) the 1,3,5-triazine derivative is at least one member selected from the group consisting of melamine, cyanuric acid, a cyanuric acid derivative, isocyanuric acid, an isocyanuric acid derivative, a melamine cyanurate and melamine isocyanurate;

(D) the phosphorus-containing compound is at least one member selected from the group consisting of red phosphorus, ammonium polyphosphate, a phosphoric acid ester, melamine phosphate, melamine polyphosphate, guanidine phosphate and ethylenediamine phosphate;

wherein a formulating ratio of (A) the ethylenediamine-containing zinc phosphate to (B) the metal compound is from 0.1 to 10 by weight ratio; and wherein a formulating ratio of the total amount of (A) the ethylenediamine-containing zinc phosphate and (B) the metal compound to (C) the 1,3,5-triazine derivative and/or (D) the phosphorus-containing compound is from 0.1 to 10 by weight ratio.

2. A flame retardant comprising (A) ethylenediamine-containing zinc phosphate, (C) a 1,3,5-triazine derivative and (D) a phosphorus-containing compound, wherein:

(C) the 1,3,5-triazine derivative is at least one member selected from the group consisting of melamine, cyanuric acid, a cyanuric acid derivative, isocyanuric acid, an isocyanuric acid derivative, melamine cyanurate and melamine isocyanurate, (D) the phosphorus-containing compound is at least one member selected from the group consisting of red phosphorus, ammonium polyphosphate, a phosphoric acid ester, melamine phosphate, melamine polyphosphate, quanidine phosphate and ethylenediamine phosphate; and wherein a formulating ratio of (A) the ethylendiamine-containing zinc phosphate to (C) the 1,3,5-triazine derivative and/or (D) the phosphorus-containing compound is from 0.1 to 10 by weight ratio.

3. The flame retardant according to claim 1, wherein the ethylenediamine-containing zinc phosphate is represented by the general formula $Zn_2P_2O_8C_2N_2H_{10}$, and the X-ray diffraction pattern of the ethylenediamine-containing zinc phosphate is one containing the following spacings:

| Spacing d (Å) | 2 θ | Relative intensity |
| --- | --- | --- |
| 7.32 ± 0.50 | 12.1 | S to M |
| 5.66 ± 0.16 | 15.6 | M |
| 4.46 ± 0.10 | 19.9 | M |
| 4.10 ± 0.10 | 21.7 | W |
| 3.81 ± 0.08 | 23.3 | S to M |
| 3.39 ± 0.07 | 26.2 | VS |
| 3.28 ± 0.05 | 27.2 | S |
| 2.76 ± 0.04 | 32.4 | W |
| 2.73 ± 0.04 | 32.8 | W |
| 2.65 ± 0.04 | 33.8 | W |
| 2.60 ± 0.04 | 34.5 | W |
| 2.31 ± 0.04 | 38.9 | W |
| 2.21 ± 0.04 | 40.9 | W |

2θ: measured by CuKα radiation (1.5405 Å), wherein in the relative intensity, VS: very strong, S: strong, M: medium, and W: weak.

4. The flame retardant according to claim 3, wherein the ethylenediamine-containing zinc phosphate is one obtained by mixing an aqueous zinc phosphate solution having a phosphorus/zinc molar ratio of from 1.0 to 2.0 with an aqueous ethylenediamine solution in an amount such that the molar ratio of ethylenediamine/zinc becomes to be from 0.5 to 1.0, then adjusting the pH to a level of from 3 to 11, followed by aging.

5. The flame retardant according to claim 1, wherein the ethylenediamine-containing zinc phosphate is represented by the general formula $Zn_2P_2O_8C_2N_2H_{10}$, and the X-ray diffraction pattern of the ethylenediamine-containing zinc phosphate is one containing the following spacings, and its particle size is less than 4 μm:

| Spacing d (Å) | 2 θ | Relative intensity |
| --- | --- | --- |
| 7.32 ± 0.50 | 12.1 | S to M |
| 5.66 ± 0.16 | 15.6 | M |
| 4.46 ± 0.10 | 19.9 | M |
| 4.10 ± 0.10 | 21.7 | W |
| 3.81 ± 0.08 | 23.3 | S to M |
| 3.39 ± 0.07 | 26.2 | VS |
| 3.28 ± 0.05 | 27.2 | S |
| 2.76 ± 0.04 | 32.4 | W |
| 2.73 ± 0.04 | 32.8 | W |
| 2.65 ± 0.04 | 33.8 | W |
| 2.60 ± 0.04 | 34.5 | W |
| 2.31 ± 0.04 | 38.9 | W |
| 2.21 ± 0.04 | 40.9 | W |

2θ: measured by CuKα radiation (1.5405 Å), wherein in the relative intensity, VS: very strong, S: strong, M: medium, and W: weak.

6. The flame retardant according to claim 5, wherein the ethylenediamine-containing zinc phosphate is one obtained by mixing an aqueous zinc phosphate solution having a phosphorus/zinc molar ratio of from 1.0 to 2.0 with an aqueous ethylenediamine solution in an amount such that the molar ratio of ethylenediamine/zinc becomes to be from 0.5 to 1.0, then adjusting the pH to a level of from 3 to 11 at a temperature of less than 40° C., followed by aging at a temperature of less than 40° C.

7. The flame retardant according to claim 1, wherein the X-ray diffraction pattern of the ethylenediamine-containing zinc phosphate is one containing the following spacings:

| Spacing d (Å) | 2 θ | Relative intensity |
| --- | --- | --- |
| 6.89 ± 0.30 | 12.8 | VS |
| 6.66 ± 0.30 | 13.3 | S |
| 4.20 ± 0.10 | 21.1 | W |

-continued

| Spacing d (Å) | 2θ | Relative intensity |
|---|---|---|
| 4.09 ± 0.10 | 21.7 | S to M |
| 3.79 ± 0.08 | 23.4 | S |
| 3.38 ± 0.07 | 26.3 | S |
| 3.32 ± 0.05 | 26.8 | W |
| 3.14 ± 0.05 | 28.4 | M |
| 2.82 ± 0.04 | 31.7 | M |
| 2.74 ± 0.04 | 32.6 | S to M |
| 2.70 ± 0.04 | 33.1 | M |
| 2.60 ± 0.04 | 34.4 | W |

2θ: measured by CuKα radiation (1.5405 Å), wherein in the relative intensity, VS: very strong, S: strong, M: medium, and W: weak.

8. The flame retardant according to claim 1, wherein the metal compound is at least one member selected from the group consisting of magnesium hydroxide, aluminum hydroxide, calcium hydroxide and zinc hydroxystannate.

9. The flame retardant according to claim 1, wherein the metal compound is at least one member selected from the group consisting of zinc oxide, nickel oxide, tin oxide, antimony oxide, zirconium oxide, molybdenum oxide, copper oxide, iron oxide, zinc borate, zinc stannate and zeolite.

10. A flame retardant resin composition comprising 100 parts by weight of a resin and from 5 to 250 parts by weight of the flame retardant as defined in claim 1.

11. The flame retardant according to claim 2, wherein the ethylenediamine-containing zinc phosphate is represented by the general formula $Zn_2P_2O_8C_2N_2H_{10}$, and the X-ray diffraction pattern of the ethylenediamine-containing zinc phosphate is one containing the following spacings:

| Spacing d (Å) | 2θ | Relative intensity |
|---|---|---|
| 7.32 ± 0.50 | 12.1 | S to M |
| 5.66 ± 0.16 | 15.6 | M |
| 4.46 ± 0.10 | 19.9 | M |
| 4.10 ± 0.10 | 21.7 | W |
| 3.81 ± 0.08 | 23.3 | S to M |
| 3.39 ± 0.07 | 26.2 | VS |
| 3.28 ± 0.05 | 27.2 | S |
| 2.76 ± 0.04 | 32.4 | W |
| 2.73 ± 0.04 | 32.8 | W |
| 2.65 ± 0.04 | 33.8 | W |
| 2.60 ± 0.04 | 34.5 | W |
| 2.31 ± 0.04 | 38.9 | W |
| 2.21 ± 0.04 | 40.9 | W |

2θ: measured by CuKα radiation (1.5405 Å), wherein in the relative intensity, VS: very strong, S: strong, M: medium, and W: weak.

12. The flame retardant according to claim 11, wherein the ethylenediamine-containing zinc phosphate is one obtained by mixing an aqueous zinc phosphate solution having a phosphorus/zinc molar ratio of from 1.0 to 2.0 with an aqueous ethylenediamine solution in an amount such that the molar ratio of ethylenediamine/zinc becomes to be from 0.5 to 1.0, then adjusting the pH to a level of from 3 to 11, followed by aging.

13. The flame retardant according to claim 2, wherein the ethylenediamine-containing zinc phosphate is represented by the general formula $Zn_2P_2O_8C_2N_2H_{10}$, and the X-ray diffraction pattern of the ethylenediamine-containing zinc phosphate is one containing the following spacings, and its particle size is less than 4 μm:

| Spacing d (Å) | 2θ | Relative intensity |
|---|---|---|
| 7.32 ± 0.50 | 12.1 | S to M |
| 5.66 ± 0.16 | 15.6 | M |
| 4.46 ± 0.10 | 19.9 | M |
| 4.10 ± 0.10 | 21.7 | W |
| 3.81 ± 0.08 | 23.3 | S to M |
| 3.39 ± 0.07 | 26.2 | VS |
| 3.28 ± 0.05 | 27.2 | S |
| 2.76 ± 0.04 | 32.4 | W |
| 2.73 ± 0.04 | 32.8 | W |
| 2.65 ± 0.04 | 33.8 | W |
| 2.60 ± 0.04 | 34.5 | W |
| 2.31 ± 0.04 | 38.9 | W |
| 2.21 ± 0.04 | 40.9 | W |

2θ: measured by CuKα radiation (1.5405 Å), wherein in the relative intensity, VS: very strong, S: strong, M: medium, and W: weak.

14. The flame retardant according to claim 1, wherein the ethylenediamine-containing zinc phosphate is one obtained by mixing an aqueous zinc phosphate solution having a phosphorus/zinc molar ratio of from 1.0 to 2.0 with an aqueous ethylenediamine solution in an amount such that the molar ratio of ethylenediamine/zinc becomes to be from 0.5 to 1.0, then adjusting the pH to a level of from 3 to 11 at a temperature of less than 40° C., followed by aging at a temperature of less than 40° C.

15. The flame retardant according to claim 2, wherein the X-ray diffraction pattern of the ethylenediamine-containing zinc phosphate is one containing the following spacings:

| Spacing d (Å) | 2θ | Relative intensity |
|---|---|---|
| 6.89 ± 0.30 | 12.8 | VS |
| 6.66 ± 0.30 | 13.3 | S |
| 4.20 ± 0.10 | 21.1 | W |
| 4.09 ± 0.10 | 21.7 | S to M |
| 3.79 ± 0.08 | 23.4 | S |
| 3.38 ± 0.07 | 26.3 | S |
| 3.32 ± 0.05 | 26.8 | W |
| 3.14 ± 0.05 | 28.4 | M |
| 2.82 ± 0.04 | 31.7 | M |
| 2.74 ± 0.04 | 32.6 | S to M |
| 2.70 ± 0.04 | 33.1 | M |
| 2.60 ± 0.04 | 34.4 | W |

2θ: measured by CuKα radiation (1.5405 Å), wherein in the relative intensity, VS: very strong, S: strong, M: medium, and W: weak.

16. The flame retardant according to claim 2, wherein the metal compound is at least one member selected from the group consisting of magnesium hydroxide, aluminum hydroxide, calcium hydroxide and zinc hydroxystannate.

17. The flame retardant according to claim 2, wherein the metal compound is at least one member selected from the group consisting of zinc oxide, nickel oxide, tin oxide, antimony oxide, zirconium oxide, molybdenum oxide, copper oxide, iron oxide, zinc borate, zinc stannate and zeolite.

18. A flame retardant resin composition comprising 100 parts by weight of a resin and from 5 to 250 parts by weight of the flame retardant as defined in claim 2.

19. The flame retardant according to claim 1, wherein a formulating ratio of the total amount of (A) the ethylendiamine-containing zinc phosphate and (D) the phosphorus-containing compound to (C) the 1,3,5-triazine derivative is from 0.1 to 10 by weight ratio.

20. The flame retardant according to claim 1, wherein:
- (B) the metal compound is at least one number selected from the group consisting of magnesium hydroxide and zinc borate;
- (C) the 1,3,5-triazine derivative is melamine cyanurate; and
- (D) the phosphorus-containing compound is at least one member selected from the group consisting of red phosphorus, ammonium polyphosphate, and melamine phosphate.

21. The flame retardant according to claim 2, wherein a formulating ratio of the total amount of (A) the ethylendiamine-containing zinc phosphate and (D) the phosphorus-containing compound to (C) the 1,3,5-triazine derivative is from 0.1 to 10 by weight ratio.

22. The flame retardant according to claim 2, wherein:
- (C) the 1,3,5-triazine derivative is melamine cyanurate, and (D) the phosphorus-containing compound is at least one member selected from the group of red phosphorus, ammonium polyphosphate, and melamine phosphate.

* * * * *